United States Patent [19]
Ladisch et al.

[11] Patent Number: 5,567,684
[45] Date of Patent: Oct. 22, 1996

[54] SYNTHETIC GANGLIOSIDE DERIVATIVES

[75] Inventors: Stephan Ladisch, Chevy Chase, Md.; Akira Hasegawa, Gifu, Japan

[73] Assignee: The Regents of The University of California, Oakland, Calif.

[21] Appl. No.: 305,832

[22] Filed: Sep. 14, 1994

[51] Int. Cl.$^6$ .......................... A61K 31/70; C08B 37/00; C07H 3/06
[52] U.S. Cl. .................. 514/25; 536/4.1; 536/17.2
[58] Field of Search ................... 536/4.1, 17.2; 514/25

[56] References Cited

U.S. PATENT DOCUMENTS

| | | | |
|---|---|---|---|
| 4,388,309 | 6/1981 | Fabricius et al. | 514/12 |
| 4,639,437 | 12/1987 | della Valle et al. | 514/54 |
| 4,849,413 | 7/1989 | della Valle et al. | 514/54 |
| 4,918,170 | 4/1990 | Hasegawa et al. | 536/17.9 |
| 5,229,373 | 7/1993 | della Valle | 514/61 |
| 5,399,567 | 3/1995 | Platt et al. | 514/315 |

FOREIGN PATENT DOCUMENTS

| | | |
|---|---|---|
| 2062369 | 9/1992 | Canada . |
| 4204889 | 9/1992 | Germany . |
| 92/17189 | 10/1992 | WIPO . |
| 93/02686 | 2/1993 | WIPO . |

OTHER PUBLICATIONS

Prokazocva, Ella, et al, Sialylated lactosylceramides, *European Journal of Biochemistry*, vol. 172, No. 1, Feb. (II) 1988, pp. 1–6.

Whisler, Ronald L. and Yates, Allan J., Regulation of Lymphocyte Responses by Human Gangliosides, *The Journal of Immunology*, vol. 125, No. 5 Nov. 1980, pp. 2106–2111.

Yates, A. J., et al, Immunological Properties of Gangliosides, *ACS Symp. Series* 128 (Cell Surf. Gylcolipids) (1980) pp. 419–433.

M. Hachida, R. Irie, and D. L. Morton, Significant Immunosuppressive Effect of Ganglioside $GM_3$ in Organ Transplantation, *Transplantation Proceedings*, Nov. 1–4, 1989 Part I, pp. 1663–1665.

Ladisch et al. *Biochem. Biophys. Res. Commun.* Sep. 15, 1994, 203(2), 1102–1109.

*Primary Examiner*—John Kight
*Assistant Examiner*—Kathleen Kahler Fonda
*Attorney, Agent, or Firm*—Poms, Smith, Lande & Rose

[57] ABSTRACT

Synthetic compounds which are useful for suppressing an immune response are disclosed. The synthetic compounds have the formula

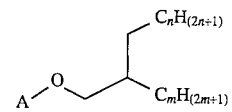

wherein A is a carbohydrate moiety which corresponds to the carbohydrate moiety of a naturally occurring ganglioside, n is 5 to 20 and m is to 20. Also presented are methods for suppressing an immune response in an animal and compositions of matter employing the compounds as shown above.

12 Claims, 4 Drawing Sheets

SYNTHETIC GANGLIOSIDE DERIVATIVES

BACKGROUND OF THE INVENTION

1. Field of the Invention

The present invention relates generally to synthetic ganglioside derivatives, not found in nature, which are useful as immunosuppressive agents. More particularly, the present invention relates to glycosphingolipids, artificial anchor gangliosides and simplified carbohydrate moiety-gangliosides which are useful pharmaceutical agents for inhibiting an immune response.

2. Description of Related Art

Although the immune response is often seen as beneficial, in certain circumstances the immune response to an antigen can actually be harmful to the animal in which the immune response occurs. An example where the immune response creates a condition wherein the host is subject to serious pathologic sequelae is in such autoimmune diseases as lupus erythematosus, rheumatoid arthritis, diabetes, and Crohn's disease. In autoimmune diseases, the immune response is directed against host tissues, and therefore use of immunosuppressive agents is a treatment approach.

Another, and one of the most important, areas which often requires substantial immunosuppression is tissue transplantation, where the suppression of the immune response is crucial in order to prevent graft rejection by the host (host versus graft reaction, HVG) and graft rejection of the host (graft versus host rejection, GVH). Typically, the tissue which is grafted is allogeneic, where the inhibition of alloreactive T lymphocytes by immunosuppressive agents is essential to the prevention of allograft rejection. Depending upon the nature of the allograft (i.e. liver, kidney, or bone marrow), the course of immunosuppressive therapy may be relatively brief (months) or may have to be continued indefinitely (years to lifetime). All of the immunosuppressive agents used thus far have significant drawbacks relating either to direct toxicity on other organ systems or to failure to provide "balanced" immunosuppression. The latter problem has two distinct aspects; on one hand inadequate suppression of the immune response can lead to rejection, while on the other hand excessive immunosuppression can allow the development of opportunistic infections and neoplasia. Thus, the need to develop an effective nontoxic immunosuppressive agent which does not cause the above severe complications continues.

At present, multi-drug therapy, including cytotoxic agents, is utilized following organ transplantation. This typically comprises combination therapy, such as treatment with cyclosporin A, azathioprine, and prednisone, the rationale being that each drug acts at a different stage in the immune response and the combination therapy will require lower doses of each individual drug, thus diminishing their dose-related side effects. However, the side effects remain significant while the efficacy of this form of therapy is still not satisfactory. Rejection continues to account for nearly 50% of graft losses in renal transplantation. And, distinguishing rejection from cyclosporin A nephrotoxicity may be difficult.

Another major cause of graft loss is systemic infection, usually by opportunistic infections, which require the tapering or cessation of immunosuppression, which leads to graft loss. Also, with such combination therapy in transplantation, there has been a significant increase in the incidence of lymphomas (Wilkinson, et al., "Transplantation," 47:293–296, 1989). The chronic failure of immunosuppressive therapy is revealed by the fact that the graft survival rate of 85% at 1 year drops to 67% at 5 years (Kahan, et al., "Am J. Kidney Dis," 5:288–295, 1985) in recipients of cadaveric renal transplants receiving triple therapy. Clearly, then the existing immunosuppressive therapy is inadequate. This has stimulated the search for, and development of, new immunosuppressive drugs, and particularly agents that are not directly toxic to either the immune system or to other organ systems. One approach to overcoming the problems associated with present immunosuppressive drugs is the use of biological agents which are actually produced by the animal. An example of such biological agents are the gangliosides.

Gangliosides are a class of glycosphingolipids. As shown schematically in FIG. 1, gangliosides have a structure containing a carbohydrate moiety linked to a ceramide. The carbohydrate moiety includes a sugar moiety which has at least one monosaccharide and one or more sialic acid moiety(s), i.e. sialic acid groups (N-acetyl or N-glycolyl neuraminic acid). FIG. 2 sets forth the nomenclature which is used to describe the ceramide moiety. The ceramide moiety includes a long chain base (LCB) portion and a fatty acid (FA) portion. The number to the left of the colon indicates the carbon chain length of the fatty acid or long chain base, and the number to the right indicates the degree of unsaturation. The major long chain base structures (to the left of the dash) of normal human brain gangliosides are d18:1 and d20:1, and of extraneural gangliosides, d18:1. The major fatty acid structures (to the right of the dash) are 18:0 and 20:0.

Gangliosides are also classified according to the number of monosaccharides in the carbohydrate moiety and the number of sialic acid groups present in the sialic acid moiety(s); Further classification is dependent upon where and how many sialic acid(s) are bound to the carbohydrate moiety. For example, the international symbol $G_{M1a}$ designates one of the more common gangliosides which has been extensively studied. The subscript, "M" in the symbol indicates that the ganglioside is a monosialoganglioside and "1" indicates that there are four saccharide units present in the carbohydrate moiety. The subscripts "a", "b" or "c" indicate isomers of the particular ganglioside described which differ in the position of the sialic acid(s). The subscripts "D", "T" and "Q" used as international ganglioside symbols represents gangliosides, trisialongangliosides and tetrasialongangliosides, respectively. The subscripts "2", "3" and "4" represent trisaccharide, disaccharide and monosaccharide gangliosides, respectively. The terminal saccharide is the saccharide which is located at the end of the carbohydrate moiety which is opposite to the end that is attached to the ceramide moiety.

Ten common human brain gangliosides and their biosynthetic pathway are set forth in the FIG. 3. The structure of each ganglioside is set forth using conventional abbreviations for the ceramide, saccharide and sialic acid (SA) groups. FIG. 3 also outlines the biosynthetic pathway of the gangliosides. The biosynthesis of gangliosides is discussed in detail in S. Roseman, *Chem. Phys. Lipids,* 5: 270–297, 1970.

It is well know that gangliosides are functionally important in the nervous system and it has been claimed that gangliosides are useful in the therapy of peripheral nervous system disorders. Numerous gangliosides are derivatives thereof have been used to treat a wide variety of nervous system disorders including cerebral ischemic strokes. For example, see U.S. Pat. Nos. 4,940,694; 4,937,232; and 4,716,223. Gangliosides have also been used to affect the activity of phagocytes (U.S. Pat. No. 4,831,021) and to treat gastrointestinal disease-producing organisms (U.S. Pat. No. 4,762,822).

The use of gangliosides and ganglioside analogues to suppress or to otherwise affect the immune system has not yet been investigated as extensively as their use in neurological disorders.

The first report of ganglioside suppression of immune responses in vivo was published twenty years ago by Agarwal and Neter, who discovered inhibition by gangliosides of the primary antibody response to bacterial antigens in mice (Agarwal, et al., *J. Immunol.*, 107: 1448–1456, 1971). Recent studies have shown that tumor gangliosides which are shed in vivo enhance tumor formation in mice (Ladisch, et al., *J.Clin.Invest.*, 79:1879–1882, 1987), a finding confirmed by other laboratories (Allessandri, et al., *Cancer Res.* 47:4243–4347, 1987; Saha, et al., *Int.J.Cancer*,41:432–435, 1988); indirect evidence (Ladisch, et al., *J. Clin. invest.*, 79:1879–1882, 1987) suggests that this enhancement occurs by an immunologic mechanism. However, a recent investigation into the in vivo immunosuppressive effect of $G_{M1}$ ganglioside or mixed bovine brain gangliosides (mainly $G_{M1}$), $G_{D1a}$, $G_{D1b}$, and $G_{T1b}$) was conducted by Presti, D. et al., (Presti, D. et al. *J. Neuroimmunology*, 22: 233–239, 1989). The study concluded that there was no evidence of a suppressive effect on humoral or cellular immunity exhibited in vivo by the $G_{M1}$ ganglioside or the mixed brain gangliosides.

As noted above, gangliosides are composed of three elements. The role these elements play, however, in the immunosuppressive activity of gangliosides is unknown. Indeed, in the past, the identification of preferred active ganglioside structures has largely been limited to naturally occurring gangliosides. Although naturally occurring gangliosides vary to some extent in the structure of their elements, the available variants do not permit a full exploration of the role the various elements play in immunosuppression.

There is, thus, a continuing need to develop chemically synthesized gangliosides, wherein the various elements of naturally occurring gangliosides are replaced with synthetic or artificial moieties.

SUMMARY OF THE INVENTION

As a first aspect of the present invention, a composition of matter is presented which comprises a glycosphingolipid which has the formula

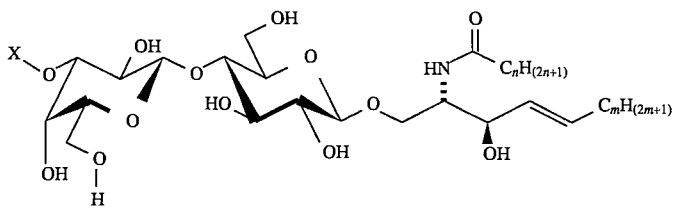

wherein x is

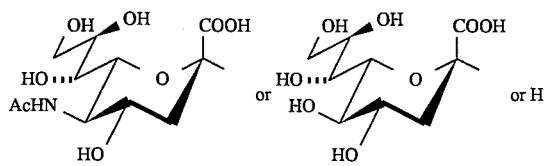

wherein Y is

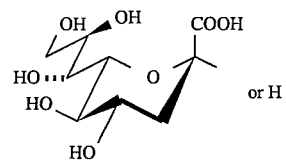

where m is 10 to 20 and wherein n is 1 to 14 and a pharmaceutically acceptable carrier for the glycosphingolipid.

This aspect of the present invention is based on the discovery that glycosphingolipids having shorter synthetic fatty acyl chains are more potent immunosuppressives than their longer fatty acyl chain counterparts. Accordingly, the shorter fatty acyl chain glycosphingolipids as set forth above are thus useful in suppressing an immune response in an animal.

In this regard, the present invention includes methods for suppressing an immune response in an animal via administration of an immune response suppressing effective amount of a glycosphingolipid according to the above formula.

Another aspect of the present invention is a synthetic ganglioside having an artificial hydrophobic anchor according to the formula

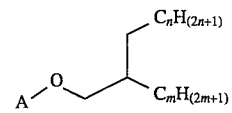

wherein A is a carbohydrate moiety of a ganglioside, n is 5 to 20 and m is 5 to 20.

This aspect of the present invention is based on the discovery in accordance with the present invention that the ceramide moiety of a ganglioside can be replaced with an artificial hydrophobic anchor structure, resulting in a highly immunosuppressive molecule. Synthetic gangliosides having artificial hydrophobic anchors in accordance with the present invention are useful for suppressing an immune response in an animal.

The present invention includes methods for suppressing an immune response in an animal via administration of an immune response suppressing effective amount of a synthetic ganglioside having an artificial hydrophobic anchor according to the above formula.

Also presented in accordance with the present invention are compositions of matter comprising a synthetic ganglioside having an artificial hydrophobic anchor according to the above formula and a pharmaceutically acceptable carrier for the synthetic ganglioside having an artificial hydrophobic anchor.

Yet another aspect of the present invention concerns a simplified carbohydrate moiety ganglioside according to the formula

[Structure: sialic acid-like sugar with OH, OH, O'H, AcHN, COOH, O—B substituents]

wherein B is a ceramide moiety of a ganglioside. This aspect of the present invention is based on the discovery in accordance with the present invention that the carbohydrate portions of a ganglioside can be simplified to a sialosyl moiety, resulting in a highly immunosuppressive agent.

Presented in accordance with this aspect of the present invention are methods for suppressing an immune response in an animal via administration of an immune response suppressing effective amount of a simplified carbohydrate moiety-ganglioside according to the above formula.

Also presented in accordance with the present invention are compositions of matter comprising a simplified carbohydrate moiety-ganglioside according to the above formula and a pharmaceutically acceptable carrier for the simplified carbohydrate moiety-ganglioside.

The above discussed and many other features and attendant advantages of the present invention will become apparent as the invention becomes better understood by reference to the following detailed description.

DETAILED DESCRIPTION OF THE PRESENT INVENTION

One aspect of the present invention involves a composition of matter comprising a glycosphingolipid having the formula

[Structure showing trisaccharide-ceramide: X-O-sugar-O-sugar-O-CH2-CH(OH)-CH(NH-C(=O)-C$_n$H$_{(2n+1)}$)-CH=CH-C$_m$H$_{(2m+1)}$]

wherein X is

[Two structures: sialic acid with AcHN or with HO] or H wherein Y is

[Structure: sugar with COOH] or H wherein m is 10 to 20 and wherein n is 1 to 14 and a pharmaceutically acceptable carrier for the glycosphingolipid. Another aspect of the present invention is a method for suppressing an immune response in an animal comprising administering an immune response suppressing effective amount of a glycosphingolipid having the above formula to an animal.

These aspects of the present invention are based on the discovery in accordance with the present invention that glycosphingolipids having shorter synthetic fatty acyl chains are more potent immunosuppressors than longer fatty acyl chain-containing glycosphingolipids of identical carbohydrate structure. For instance, a glycosphingolipid according to the above formula wherein n=1 was found in accordance with the present invention to have greater immunosuppressive activity than glycosphingolipids wherein n is 17 or 23. Other species of glycosphingolipids wherein n is 1 to 14 and wherein m is 10 to 20 are also expected to have higher immunosuppressive activity than their longer fatty acyl chain-containing counterparts. Thus, ceramide moieties with shorter fatty acyl chains, as defined above may be linked to a carbohydrate moiety corresponding to that of any naturally occurring ganglioside.

Preferably, in a glycosphingolipid according to the methods and compositions of matter of the present invention, m is 13 and n is from 1 to 5. Most preferably, m is 13 and n is 1. This is also the case with regard to the compositions of matter and methods employing a glycosphingolipid as disclosed in accordance with the instant invention.

In a preferred exemplary glycosphingolipid according to the present invention, X is preferably

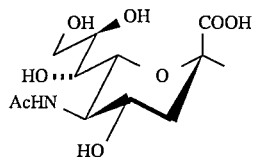

and Y is preferably H. Further, when X and Y are as described in this paragraph, m is preferably 13 and n is preferably from 1–5. Most preferably, X and Y are as described in this paragraph, m is 13 and n is 1. Gangliosides containing a synthetic fatty acyl structure in accordance with the present invention are synthesized according to methods well known to those of skill in the art. See, e.g., Murase et al. (1989) Carbohydr. Res. 188, 71–80; KDN analogs are synthesized according to Terada, et al. (1993) J. Carbohydr. Chem. 12, 425–440.

Another aspect of the present invention is a synthetic ganglioside having an artificial hydrophobic anchor according to the formula

Figure 1:
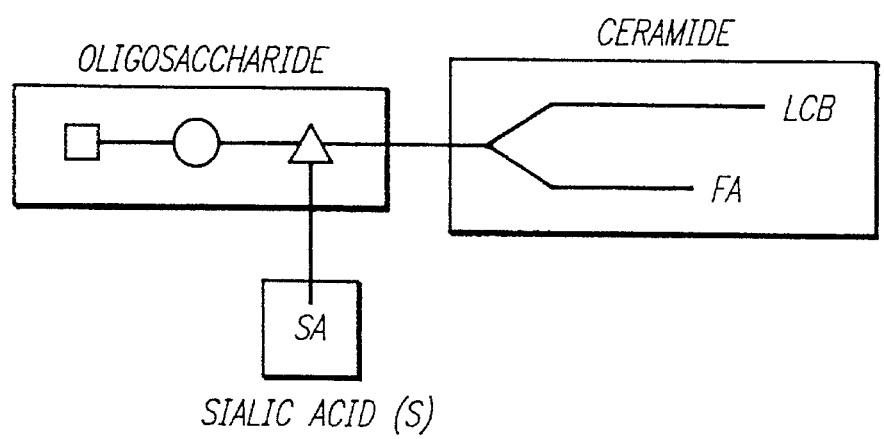
FIG. 1 depicts the structure of a ganglioside.
Figure 2:
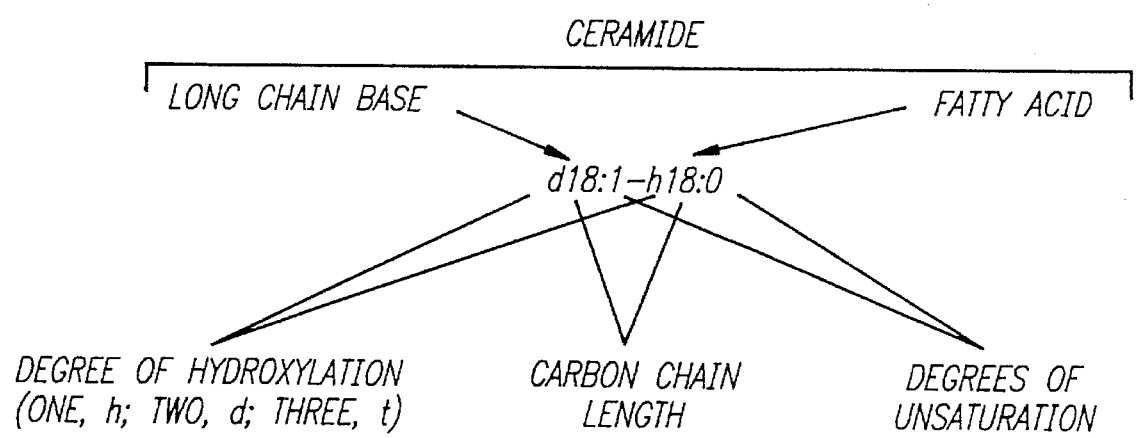
FIG. 2 depicts the structure and nomenclature of the ceramide portion of a ganglioside.
Figure 3:
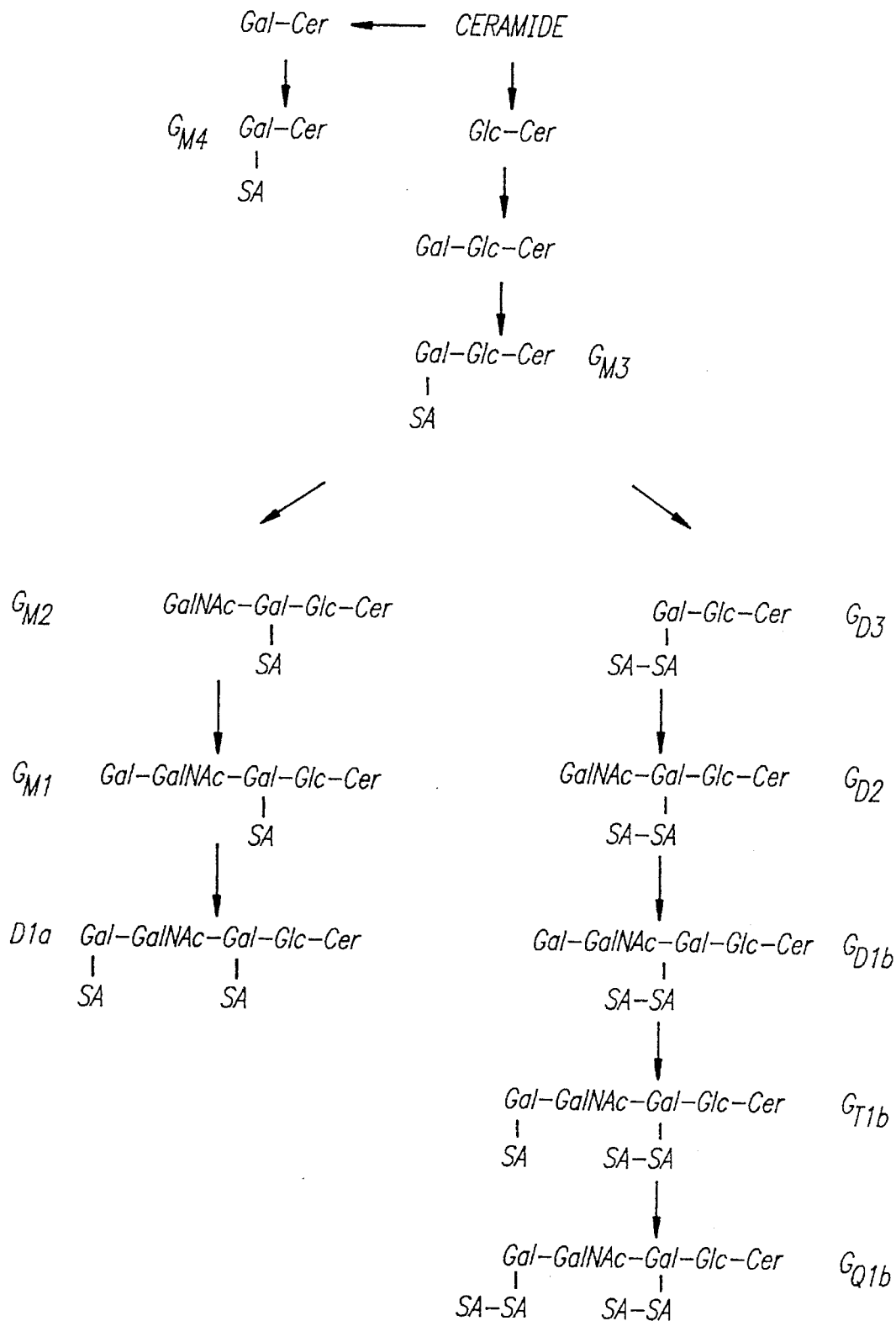
FIG. 3 depicts the carbohydrate structure and biosynthetic pathway of 10 naturally occurring gangliosides.

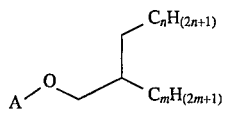

wherein A is a carbohydrate moiety which corresponds to the carbohydrate moiety of a naturally occurring ganglioside, n is 5 to 20 and m is 5 to 20. As used with respect to the present invention, "carbohydrate moiety" includes both the oligosaccharide core, and any attendant sialic acid residues of any naturally occurring ganglioside as shown in FIG. 2. Exemplary carbohydrate moieties from which A may be selected include those shown in FIG. 3. Two other aspects of the present invention are a composition of matter comprising a synthetic ganglioside having an artificial hydrophobic anchor according to the formula set forth in this paragraph and a pharmaceutically acceptable carrier for the synthetic ganglioside; and a method of suppressing an immune response in an animal comprising the step of administering an immune response suppressing effective amount of a synthetic ganglioside according to the formula set forth in this paragraph.

This aspect of the present invention is based on the discovery in accordance with the present invention that the ceramide moiety of a ganglioside can be replaced with an artificial hydrophobic anchor structure, resulting in an immunosuppressive agent more potent than naturally occurring gangliosides. Other artificial hydrophobic anchor sequences may also be used in accordance with the present invention, including, for example, those containing additional methylene groups between the oxygen atom and the alkane chains as shown in the above formula.

In a synthetic ganglioside having an artificial hydrophobic anchor according to the present invention, n is preferably 13. Further, m is preferably 14. Most preferably n is 13 and m is 14.

In a synthetic ganglioside having an artificial hydrophobic anchor in accordance with the present invention, A is preferably

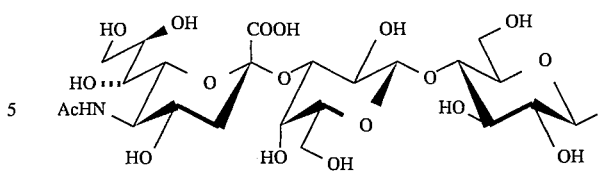

In the most preferred exemplary embodiment of the present invention, A is as shown above, n is 13 and m is 14.

The preferred embodiments of the synthetic gangliosides having an artificial hydrophobic anchor are also the preferred embodiments for its related compositions of matter and methods of suppressing an immune response in an animal.

Synthetic gangliosides having an artificial hydrophobic anchor, in accordance with the present invention, may generally be synthesized according to the methodologies employed with respect to the synthesis of a synthetic ganglioside having an artificial hydrophobic anchor as set forth in the examples.

Carbohydrate moieties are synthesized according to the following references: T. Murase, A. Kameyama, K. P. R. Kartha, H. Ishida, M. Kiso, and A. Hasegawa, J. Carbohydr. Chem., 8, 265 (1989). T. Murase, H. Ishida, M. Kiso, and A. Hasegawa, Carbohydr. Res., 188, 71 (1989); A. Hasegawa, T. Murase, K. Adachi, M. Morita, and M. Kiso, J. Carbohydr. Chem., J. Carbohydr. Chem., 9, 181 (1990); A. Hasegawa, T. Murase, M. Morita, H. Ishida, and M. Kiso, J. Carbohydr. Chem., 9, 201 (1990). T. Terada, M. Kiso, and A. Hasegawa, J. Carbohydr. Chem., 12, 425 (1993); T. Terada, M. Kiso, and A. Hasegawa, Carbohydr. Res., 259, 201 (1994); Carbohydrates—Synthetic Methods and Applications in Medicinal Chemistry—pp 243–266 (1992) Eds. by H. Ogura, A. Hasegawa, and T. Suami, Kodansha-VCH; Synthetic Oligosaccharide—Indispensable Probes for the Life Sciences—Ed. by P. Kovac, ACS Symposium Series 560, American Chemical Society, pp. 184–197 (1994), by A. Hasegawa.

Yet another aspect of the present invention is a simplified carbohydrate-moiety ganglioside according to the formula

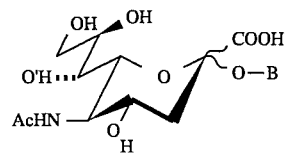

wherein B is a ceramide moiety which corresponds to the ceramide moiety present in a naturally occurring ganglioside. Exemplary ceramide moieties from which B may be selected include, using the nomenclature of FIG. 2, those with a long chain base of d18:1 or d20:1 in combination with any of the following: C16:0, C18:0, C20:0, C22:0, C24:0 and C24:1. In addition, synthetic ceramide moieties, as disclosed herein with respect to the glycosphingolipid aspect of the present invention, are also expected to provide potent immunosuppressors when linked to a sialosyl residue as disclosed above. Examples of these synthetic ceramide groups include C2:0, C10:0 and C14:0.

Two other related aspects of the present invention are a composition of matter comprising a simplified carbohydrate moiety-ganglioside according to the above formula and a pharmaceutically acceptable carrier for the simplified carbohydrate moiety-ganglioside; and a method for suppressing an immune response in an animal comprising the step of administering to the animal an immune response suppressing effective-amount of a simplified carbohydrate moiety-ganglioside according to the above formula.

The simplified carbohydrate moiety-ganglioside aspect of the present invention is based on the discovery in accordance with the present invention that the carbohydrate portion of a ganglioside can be simplified to a sialosyl moiety resulting in a highly effective immunosuppressive agent.

In a simplified carbohydrate-moiety ganglioside according to the present invention, B is preferably $$\text{structure with OH, NHCOC}_{17}\text{H}_{35}\text{, and C}_{13}\text{H}_{27}$$

This is also the preferred embodiment for the method and composition of matter employing a simplified carbohydrate moiety-ganglioside.

Simplified carbohydrate moiety-gangliosides, in accordance with the present invention, may generally be synthesized according to the methodologies set forth with respect to the synthesis of a specific simplified carbohydrate moiety-ganglioside as set forth in the examples. Ceramide moieties are generally synthesized according to Ito, et al., J. Carbohyudr., Chem., 6, 117 (1987).

As demonstrated in the examples below, the glycosphingolipids, artificial anchor gangliosides, and simplified carbohydrate moiety-ganglioside and their corresponding compositions of matter are potent immunosuppressive agents and they are useful for treating animals, including humans, where it is desirous to reduce an immune response. It is desirous to reduce an immune response, for example, in order to inhibit rejection of a tissue graft.

In the present invention, the term "suppressive" denotes a lessening of the detrimental effect of the undesirable immune response in the animal receiving therapy. The term "immune response suppressing effective amount" means that the amount of agent used is of sufficient quantity to suppress the cause of disease or symptoms due to the undesirable immune response. The term "animal" also denotes humans.

The dosage ranges for the glycosphingolipids, artificial anchor gangliosides and simplified carbohydrate moiety-gangliosides ("immunosuppressive agents") of the present invention are those large enough to produce the desired effect: the immune response shows some degree of suppression. The dosage should not be so large as to cause adverse side effects. Generally, the dosage will vary with the age, condition, sex and extent of the disease in the animal and can be determined by one of skill in the art. The dosage can be adjusted by the individual physician in the event of any counterindications. Dosage can vary from less than 1 mg/kg/dose to about 100 mg/kg/dose, preferably about 5 mg/kg/dose to 10 mg/kg/dose, in one or more dose administrations daily.

The immunosuppressive agents of the present invention can be administered parenterally by single injections or by gradual infusion over time. The immunosuppressive agents can also be administered intravenously, intraperitoneally, intramuscularly, subcutaneously, intracavitarily, or transdermally.

Pharmaceutically acceptable carriers include sterile aqueous or non-aqueous solutions, suspensions, and emulsions. Examples of non-aqueous solvents are propylene glycol., polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils, intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Additional pharmaceutical methods may be employed to control the duration of action. Controlled release preparations may be achieved by the use of polymers to complex or adsorb the immunosuppressive agents of the present invention. The controlled delivery may be exercised by selecting appropriate macromolecules (for example, polyesters, polyamino carboxymethylcellulose, and protamine sulfate) and the concentration of macromolecules as well as the methods of incorporation in order to control release. Another possible method to control the duration of action by controlled release preparations is to incorporate the immunosuppressive agents of the present invention into particles of a polymeric material such as polyesters, polyamino acids, hydrogels, poly (lactic acid) or ethylene vinylacetate copolymers.

In order to protect the immunosuppressive agents from binding with plasma proteins, it is preferred that the gangliosides be entrapped in microcapsules prepared, for example, by coacervation techniques or by interfacial polymerization, for example, hydroxymethylcellulose or gelatin-microcapsules and poly(Methymethacrylate) microcapsules, respectively, or in colloidal drug delivery systems, for example, liposomes, albumin microspheres, microemulsions, nanoparticles, and nonacapsules or in macroemulsions. Such teachings are disclosed in *Remington's Pharmaceutical Sciences* (16th Ed., A. Oslo, ed., Mack, Easton, Pa., 1980).

The immunosuppressive agents of the present invention are well suited for use in targetable drug delivery systems such as synthetic or natural polymers in the form of macromolecular complexes, nanocapsules, microspheres, or beads, and lipid-based systems including oil-in-water emulsions, liposomes, and resealed erythrocytes. Miscelles and mixed micelles are particularly preferred for delivering the immunosuppressive agents of the present invention. These systems are known collectively as colloidal drug delivery systems. Typically such colloidal particles containing the dispersed gangliosides are about 50 nm–2 μm in diameter. The size of the colloidal particles allows them to be administered intravenously such as by injection, or as an aerosol. Materials used in the preparation of colloidal systems are typically sterillzable via filter sterilization, nontoxic, and biodegradable, for example albumin, ethylcellulose, casein, gelatin, lecithin, phospholipids, and soybean oil. Polymeric colloidal systems are prepared by a process similar to the coacervation of microencapsulation.

Most preferred as a targeted delivery system for the immunosuppressive agents of the present invention are liposomes. When phospholipids are gently dispersed in aqueous media, they swell, hydrate, and spontaneously form multilamellar concentric bilayer vesicles with layers of aqueous media separating the lipid bilayer. Such systems are usually referred to as multilamellar liposomes or multilamellar vesicles (MLVs) and have diameters ranging from about 100nm to about 4 um. When MLVs are sonicated, small unilamellar vesicles (SUVs) with diameters in the range of from about 20 to about 50 nm are formed, which contain an aqueous solution in the core of the SUV.

The composition of the liposome is usually a combination of phospholipids, particularly high-phase-transition-temperature phospholipids, usually in combination with steroids, especially cholesterol. Other phospholipids or other lipids may also be used.

Examples of lipids useful in liposome production include phosphatidyl compounds, such as phosphatidylglycerol, phosphatidylcholine, phosphatidyserine, and phosphatidylethanolamine. Particularly useful are diacylphosphatidylglycerols, where the lipid moiety contains from 14–18 carbon atoms, particularly from 16–18 carbon atoms, and are saturated. Illustrative phospholipids include egg phosphatidylcholine, dipalmitoylphosphatidylcholine, and distearoylphosphatidylcholine.

In preparing liposomes containing the immunosuppressive agents of the present invention, such variables as the efficiency of ganglioside encapsulation, lability of the ganglioside, homogeneity and size of the resulting population of liposomes, immunosuppressive agent-to-lipid ratio, permeability instability of the preparation, and pharmaceutical acceptability of the formulation should be considered. Szoka, et al., Annual Review of Biophyusics and Bioengineering, 9:467, 1980; Deamer, et al., in Liposomes, Marcel Dekker, New York, 1983, 27: Hope, et al., Chem. Phys. Lipids, 40:89, 1986).

The targeting of liposomes has been classified based on anatomical and mechanistic factors. Anatomical classification is based on the level of selectivity, for example, organ-specific, cell-specific, and organelle-specific. Mechanistic targeting can be further distinguished based upon whether it is passive or active. Passive targeting utilizes the natural tendency of liposomes to distribute to cells of the reticuloendothelian systems (RES) in organs which contain sinusoidal capillaries. Active targeting, on the other hand, involves the alteration of the liposome by coupling the liposome to a specific ligand such as a monoclonal antibody, sugar, glycolipid, or protein, or by changing the composition or size of the liposomes themselves in order to achieve targeting to organs-and-cell types other than the naturally occurring sites of localization. Alternatively, liposomes may physically localize in capillary beds such as the lung or may be given by site-specific injection.

Another targeted delivery system which can be used with the immunosuppressive agents of the present invention is resealed erythrocytes. When erythrocytes are suspended in a hypotonic medium, swelling occurs and the cell membrane ruptures. As a consequence, pores are formed with diameters of approximately 200–500 A which allow equilibration of the intracellular and extracellular environment. If the ionic strength Of this surrounding media is then adjusted to isotonic conditions and the cells incubated at 37° C., the pores will close such that the erythrocyte reseals. This technique can be utilized with the immunosuppressive agents of the present invention to entrap the immunosuppressive agent inside the resealed erythrocyte. The resealed erythrocyte containing the immunosuppressive agent can them be used for targeted delivery.

The targeted delivery system containing the immunosuppressive agents of the present invention may be administered in a variety of ways to a host, particularly a mammalian host, such as intravenously, intramuscularly, subcutaneously, intra-peritoneally, intravascularly, topically, intracavitarily, transdermally, intranasally, and by inhalation. The concentration of the gangliosides will vary upon the particular application, the nature of the disease, the frequency of administration, or the like. The targeted delivery system-encapsulated ganglioside may be provided in a formulation comprising other compounds as appropriate and an aqueous physiologically acceptable medium, for example, saline, phosphate buffered saline, or the like.

The above disclosure generally describes the present invention. A further understanding can be obtained by reference to the following specific examples which are provided for purposes of illustration and are not intended to be limiting.

EXAMPLES

GLYCOSPHINGOLIPIDS WITH REDUCED FATTY ACYL CHAIN LENGTH EXHIBIT ENHANCED IMMUNOSUPPRESSIVE ACTIVITY

In this example, the immunosuppressive activity of glycosphingolipids with reduced fatty acyl chain length were compared to that of their longer fatty acyl chain containing counterparts.

Glycosphingolipids according to the structure

[Chemical structure showing glycosphingolipid with $C_nH_{(2n+1)}$ and $C_mH_{(2m+1)}$ groups]

wherein x is

[Chemical structure showing sialic acid moiety with OH, COOH, AcHN groups]

wherein Y is H wherein m is 13 and wherein n is either −1 (a lyso glycosphingolipid, having no fatty acyl portion), 1, 13, 17 or 23, were tested for their immunosuppressive activity. The carbohydrate portion of the studied glycosphingolipids corresponds to that of $G_{M3}$ and, thus, the studied glycosphingolipids are also referred to as $G_{M3}$ n=a number from −1 to 23.

Materials and Methods

Lymphocyte proliferation assay: An assay of the human cellular immune response, lymphoproliferation stimulated by a specific antigen, tetanus toxoid (Ladisch et al., Brochim Briphys. Aota, 1125, 180–88 (1992), has been used to measure the immunosuppressive effects of the synthetic ganglioside derivatives of the present invention. Briefly, normal human peripheral blood mononuclear leukocytes were isolated by Ficoll-hypaque density gradient centrifugation (Boyum, Scand. J. Clin. Lab. Invest 21, 77–89 (1968) from whole blood collected in preservative-free heparin (50 U/ml). The cells were washed three times and resuspended in complete HB104 medium. Autologous human plasma was added to a final concentration of 0.5%. Normal human peripheral blood mononuclear leukocytes were cultured in 96-well (A/2) tissue culture clusters (Costar No. 3696).

Synthetic ganglioside derivatives were suspended in medium by brief sonication before addition to the cell cultures. 10 μl synthetic ganglioside derivative solution were added per well, followed by addition of the peripheral blood mononuclear leukocytes (PBMC, 25 μl, 2×10⁶ cells/ml complete medium). After a 3 h preincubation at 37° C., 10 µl of the previously determined optimal concentration of the stimulant of lymphoproliferation, tetanus toxoid (3.5 Lf/ml, Mass. Dept. of Health, Boston, Mass.) was added. 10 µl of basal medium alone was added to unstimulated control cultures. The complete cultures were incubated at 37° C. in 95% air/5% $CO_2$ for 6 days Biochem. Biophys. Aota 1125, 180–88 (1992). As has been previously documented under these conditions Biochem. Biophys,. Aota 1125m 180–88 (1992), gangliosides are not toxic to the cells. At the end of the culture period, 0.5 µCi [$^3$H]thymidine in 50 µl medium was added to each well. The cultures were incubated for an additional 4.5 h and harvested onto glass fiber filter paper. Cellular [$^3$H]thymidine uptake was quantified by β-scintillation counting. Mean net [$^3$H]thymidine uptake in stimulated cultures was determined by subtracting the mean cpm of unstimulated cultures. Percent inhibition was calculated by comparing the mean net [$^3$H]thymidine uptake of cultures containing gangliosides with that of cultures without synthetic ganglioside derivatives.

In vivo Assay of Immunosuppressive Activity: Footpad injection of the synthetic ganglioside derivatives being studied and of the stimulant of the cellular immune response (allogeneic cells), is subsequently followed by harvest of the popliteal node and assessment of the node size, cell number, specific proliferation response and generation of specific cytotoxicity.

Mice: C3H (H-$2^K$) and BALB/c (H-$2^d$) mice are obtained at 6 weeks of age and used in these experiments at 7–12 weeks of age. The animals are murine virus free strains purchased from Charles River, Wilmington, Mass.

Preparation of stimulator cells: Spleens are removed aseptically and immediately placed in murine complete media [RPMI 1640 w/o L-glutamine (Whittaker Bioproducts, Walkersville, Md.) supplemented with 10% FCS; 1% of MEM non-essential amino acids (Cellgro), sodium pyruvate, L-glutamine, Penicillin 50 U/ml/Streptomycin 50 µg/ml and 10 mM Hepes Buffer (Whittaker Bioproducts)] then transferred to a 60×10 mm petri dish. A sterile single cell suspension is prepared by gently pressing the spleen onto a cell dissociation sieve (Sigma). Mononuclear cells are isolated by Ficoll-Hypaque density gradient separation, followed by lysis of erythrocytes (ACK lysing buffer pH 7.4). The cells are washed and their viability determined by trypan blue exclusion. Allogeneic (BALB/c) splenocytes are diluted to the appropriate concentration in saline and are injected into the footpad of C3H mice together with the synthetic ganglioside derivatives to be tested.

Preparation of synthetic ganglioside derivatives: Synthetic ganglioside derivatives are aliquoted in HPLC-grade chloroform:methanol (1:1), and dried in glass microvials. The synthetic ganglioside derivatives are then resuspended for injection in 0.9% NaCl, sonicated for 2 min in a Branson water bath sonicator.

Injections: Spleen cells or tumor cells and the synthetic ganglioside derivatives being studied are injected into the left hind footpad in a total volume of 30 µl. Cyclosporin A is administered i.p.

Isolation of popliteal lymph nodes: Primed animals are killed by cervical dislocation on day 4, the popliteal lymph node draining the left and right footpads are removed aseptically, trimmed free of excess fat, weighted and placed on ice in tubes containing tissue culture medium. The nodes are then teased with a flat end of a 3 ml syringe to obtain a single cell suspension, which is washed in complete murine media containing 0.1% 2mercaptoethanol (Gibco, New York). The cells are then quantified and their viability determined by trypan blue exclusion. The cell concentration is adjusted to 2×10$^6$ cells/ml.

Cell cultures: 2×10$^5$ lymph node cells in 100 µl are cultured for 18 hours in complete medium with 0.5 µC $^3$H-thymidine incorporation quantified by β-scintillation counting as a measure of in vivo lymphocyte activation (50).

RESULTS

Figure 4:
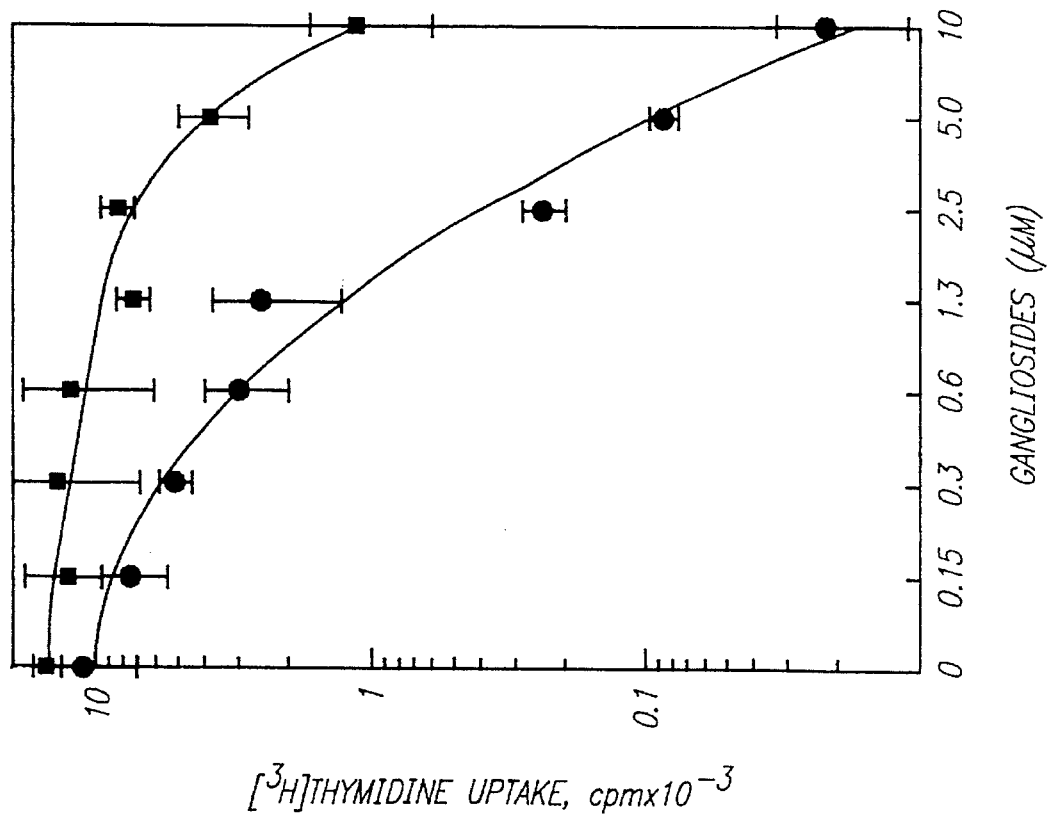
FIG. 4 is a graphical representation of the inhibition of the human lymphoproliferative response ($^3$H-thymidine uptake) by $G_{M3}$N=1 (●) and lyso $G_{M3}$ (■).

Role of ceramide structure in determining immunosuppressive activity of glycosphingolipids: The activities of two synthetic glycosphingolipids, $G_{M3}$ n=1 and $G_{M3}$ n=−1 (lyso $G_{M3}$) were compared at various concentrations for their inhibition of the human lymophoproliferative response (FIG. 4). Each point in FIG. 4 represents the mean±SEM of triplicate cultures, control stimulation was 11.5±3.0×10$^3$ CPM. The importance of a fatty acyl structure was evidenced by the higher degree of immunosuppressive activity of the glycosphingolipid wherein n=1 ($ID_{50}$=0.2 nm), compared to that of the glycosphingolipid wherein n=−1 (lyso $G_{M3}$) (FIG. 4).

Figure 5:
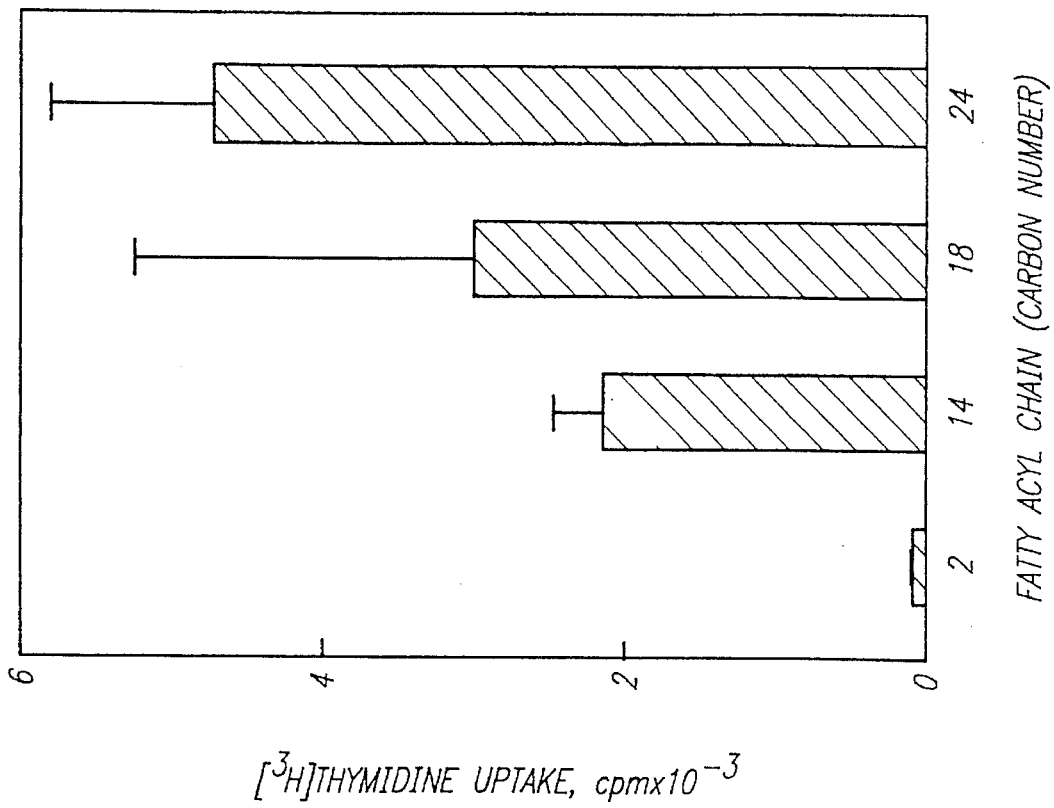
FIG. 5 is a bar graph showing inhibition of the human lymphoproliferative response by $G_{M3}$ n=1, n=13, n=17, and n=23.

Next, the relative immunosuppressive activities of a number of glycosphingolipids were compared: $G_{M3}$ (n=1, n=13, n=17 and n=23), (FIG. 5). Each bar represents the mean±SEM [$^3$H]thymidine uptake of cultures exposed to 5 µM of the indicated $G_{M3}$ species. Control stimulation= 11.5±3.0×10$^3$ cpm. The tested glycosphingolipids exhibited an immunosuppressive effect which increased as the length of the fatty acyl portion decreased, with n=1 having the highest immunosuppressive activity.

$G_{M3}$ n=1 was also tested for immunosuppressive activity in vivo. A single dose of $G_{M3}$ n=1 was found to be almost as immunosuppressive as systemically administered cyclosporin A, a known immunosuppressant (Table 1). The in vivo immunosuppressive activity of $G_{M3}$ n=1 was also compared to that of mixed human brain gangliosides; $G_{M3}$ n=1 was found to be much more active than the mixed brain gangliosides.

TABLE 1

| Parameter | Control | Cyclosporin A | $G_{M3}$ n = 1 |
|---|---|---|---|
| lymph node mass, mg[1] | | | |
| unstimulated | 1.17 ± 0.17 | 0.99 ± 0.34 | 1.29 ± 0.24 |
| stimulated | 2.77 ± 0.53 | 1.26 ± 0.22 | 1.84 ± 0.30 |
| net increase | 1.60 ± 0.46 | 0.27 ± 0.48 | 0.56 ± 0.36 |
| lymphocytes × 10$^{7[2]}$ | 2.26 | 0.30 | 1.03 |
| [$^3$H]thymidine uptake, cpm[3] | 1108 ± 283 | 201 ± 18 | 329 ± 18 |

[1]Synthetic ganglioside $G_{m3}$ n = 1 (10 nmol) was coinjected into the left hind footpad of C3H mice together with allogeneic splenocytes (BALB/C, 2.5 × 10$^6$), which was compared with the systemic administered cyclosporin A (24 mg/kg/dose i.p. × 4 doses). On day 4, the popliteal lymph nodes draining the left (stimulated) and the right footpad (unstimulated) were removed, and the lymph node mass measured. The data represent the mean ± SD of five mice in each group in this representative experiment. The difference in the net increase of popliteal nodes between control and $G_{M3}$ n = 1 treated groups is statistically significant (P < 0.01).
[2]The total mononuclear leukocytes recovered from five stimulated popliteal lymph nodes of five mice in each group.
[3]The spontaneous lymphoproliferation was measured by cellular [$^3$H]thymidine incorporation at the cell density of 2 × 10$^5$ cells/well. The data represent the mean ± SD of three cultures.

IMMUNOSUPPRESSIVE PROPERTIES OF AN ARTIFICIAL ANCHOR GANGLIOSIDE

In this example, a synthetic ganglioside having an artificial hydrophobic anchor having the structure

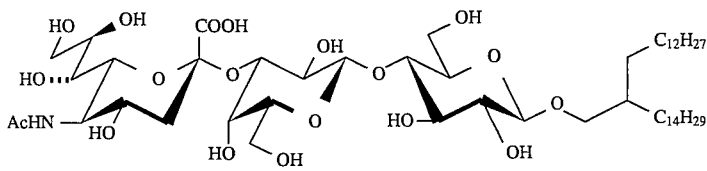

was tested to determine whether it was immunosuppressive. This compound has a carbohydrate portion corresponding to $G_{M3}$ and is also referred to as dialkyl $G_{M3}$.

Materials and Methods

Synthesis of dialkyl $G_{M3}$:

Dialkyl $G_{M3}$ was synthesized according to the following general strategy:

B. Synthesis of 2-(Tetradecylhexadecyl) O-(5-acetamido-3,5 -dideoxy-D-glycero-D-galacto-2-nonulopyranosylonic acid)-(2→3)-O-β-D-galactopyranosyl-(1→4)-β-D-glucopyranoside (4 from general strategy).

To a solution of 3 (75 mg, 0.045 mmol) in methanol (5 mL) were added 5 drops of 28% sodium methoxide solution in methanol, and the mixture was stirred for 10 h at room

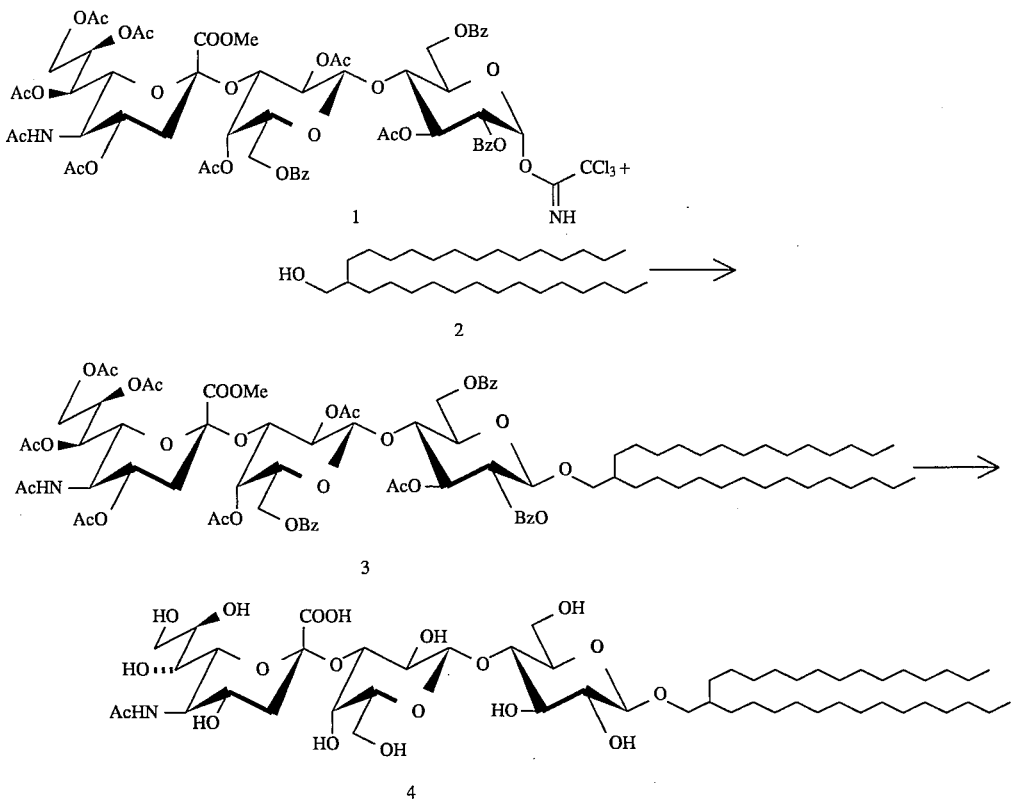

A. Synthesis of 2-(Tetradecylhexadecyl) O-(methyl 5-acetamido-4,7,8,9-tetra-O-acetyl-3,5-dideoxy-D-glycero-α-D-galacto-2-nonulopyranosylonate)-(2→3))-O-(2,4-di-O-acetyl-6-O-benzoyl-β-D-galactopyranosyl)-(1→4)- 3-O-acetyl-2,6-di-O-benzoyl-β-D-glucopyranoside (3 from general strategy set forth above).

To a solution of the trichloracetimidate (Murase, et al. Carbohydr. Res.188, 71–80(1989) (1; 150 mg, 0.11 mmol) and 2-tetradecylheadecyl-1-ol (2; 120 mg, 0.27 mmol) in $CH_2Cl_2$ (3 mL) was added molecular sieves 4A, AW 300 (2 g), and the mixture was stirred for 30 min., then cooled to 0° C. Boron trifluoride etherate (0.04 mL) was added to this mixture, and this was stirred for 4 h at 0° C. and filtered. Dichloromethane (50 mL) was added to the filtrate, and this was washed with $MNa_2CO_3$ and water, dried ($Na_2SO_4$) and evaporated. Column chromatography of the residue on silica gel (30 g) with 3:2 ethyl acetate-hexane gave 3 (0.16 g, 89%) as an amorphous mass.

temperature, and then water (0.5 mL) was added. The solution was stirred for another 8 h and neutralized with Amberlite IR-120($H^+$) resin, then concentrated. Column chromatography (MeOH) of the residue on Sephadex LH-20 (30 g) gave 4 (quantitative) as an amorphous mass.

C. Synthesis of 2-Tetradecylhexadecyl-1-O1(2 from general strategy)

Compound 2 was obtained as an amorphous mass from 2-tetradecyl-hexadecanoic acid via methyl esterification and subsequent reduction of the methyl ester with $LiAlH_4$.

Assays: In vivo and in vitro assays of immunosuppression were as described above.

Quantitative and qualitative analysis of dialkyl $G_{M3}$: Dialkyl $G_{M3}$ was quantified by resorcinol assay Svennerholm, Biochem. Biophys. Acta 24, 604–611 (1957) and analyzed by high performance-TLC. The developing solvent system was chloroform/methanol/0.2% $CaCl_2$ $2H_2O$ (60:40:9, by volume), and the glycoconjugates were stained by resorcinol-HCl Ledeen et al., *Methods Enzymol,* 83, 139–191 (1982).

Results

Figure 7:
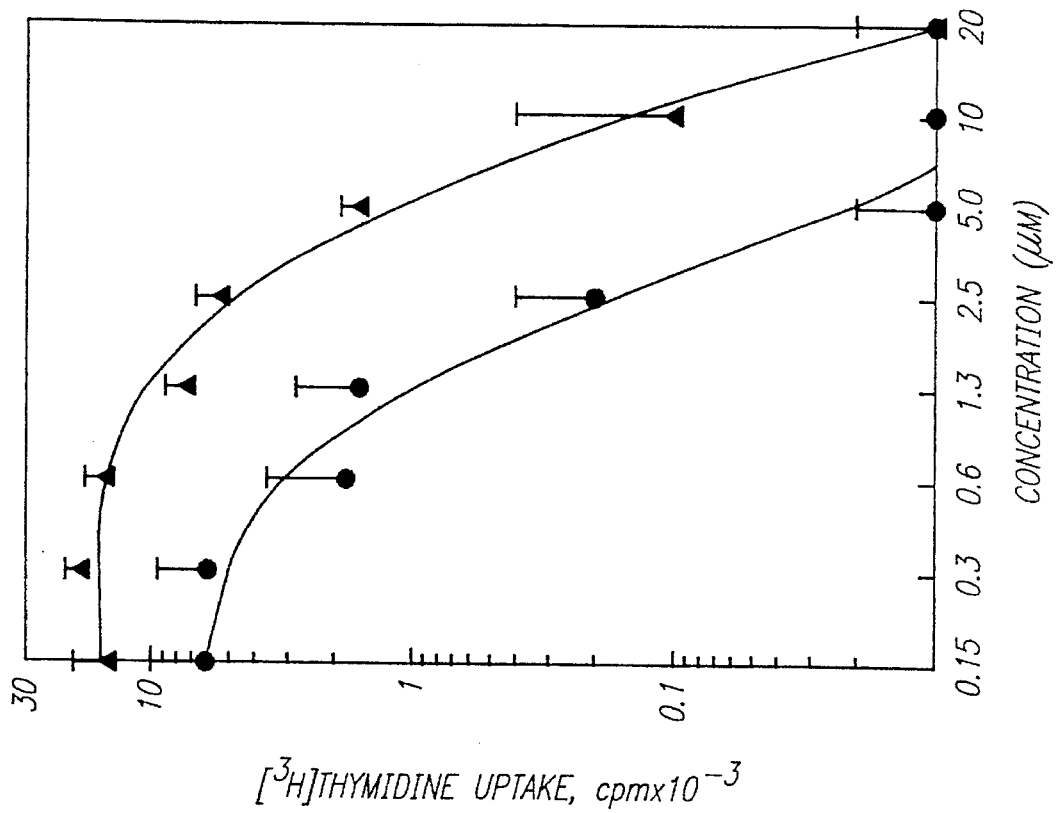
FIG. 7 is a graphical representation of the inhibition of the human lymphoproliferative response ($^3$H-thymidine uptake) by dialkyl $G_{M3}$ (●) and d 18:1-C18:0 $G_{M3}$ (▲).
Figure 6:
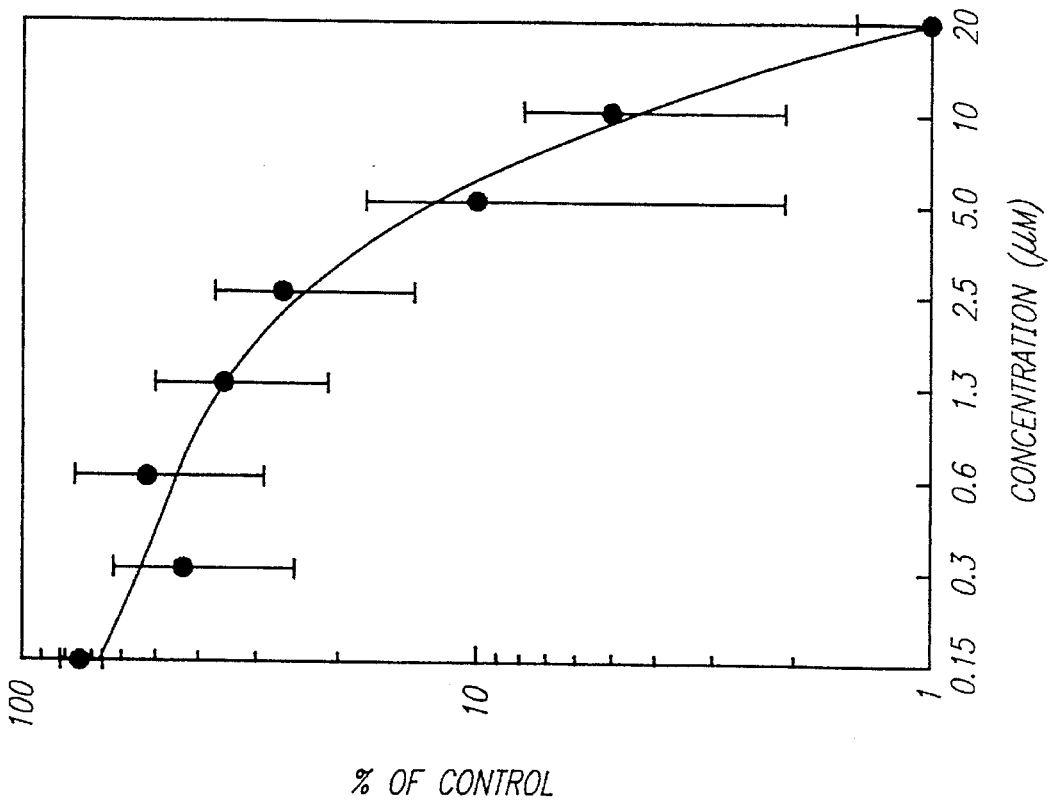
FIG. 6 is a graphical representation of the inhibition of the human lymphoproliferative response ($^3$H-thymidine uptake) by dialkyl $G_{M3}$.

Immunosuppressive activity of dialkyl $G_{M3}$: Chemically synthesized dialkyl $G_{M3}$ was assessed for its immunosuppressive activity in a tetanus toxoid-induced human lymphoproliferation assay over a range of glycoconjugate concentrations (0–20 μM). The % inhibition of cellular proliferation by glycoconjugate-treated cultures was calculated in five separate experiments by comparing the mean net [$^3$H]thymidine uptake of triplicate glycoconjugate-treated cultures with control cultures. Each point represents the mean inhibition±SD in three experiments. Control stimulation was 2.2±0.6×10$^4$ cpm. the ID$_{50}$ for dialkyl $G_{M3}$ was less than 0.3 μM. As shown in FIG. 6, dialkyl $G_{M3}$ has marked immunosuppressive activity. The concentration causing 50% inhibition of the antigen-induced human lymphoproliferative response (ID$_{50}$), was less than 1 μM, and 90% inhibition was observed at <7 μM. When these high degrees of inhibition were compared with those obtained by $G_{M3}$ (d:18:1-C18:0) in parallel experiments, one of the naturally occurring species of $G_{M3}$ which was also obtained by chemical synthesis, the higher degree of inhibition of dialkyl $G_{M3}$ than that of $G_{M3}$ is readily observed. Chemically synthesized dialkyl $G_{M3}$ (●) and d18:1-C18:0 $G_{M3}$ (▲) were assessed for immunosuppressive activity in the tetanus toxoid-induced human lymphoproliferation assay over a range of ganglioside concentrations (0–10 μM). Each point represents the mean±SEM of triplicate cultures. Control stimulation was 1.6±0.4×10$^4$ cpm. Dialkyl $G_{M3}$ had an ID$_{50}$ of 0.2 μM, and was four-fold more potent than $G_{M3}$ D18:1-c18:0 (FIG. 7). These results demonstrate that the chemically synthesized dialkyl $G_{M3}$ strongly inhibits the human cellular immune response in vitro, as measured by tetanus toxoid-induced lymphoproliferation.

Inhibition of the allogeneic immune response in vivo: To determine the potential significance of the in vitro immunosuppressive activity of dialkyl $G_{M3}$ which is shown by FIGS. 6 and 7, a murine model was used to evaluate the in vivo immunosuppressive activity of dialkyl $G_{M3}$. In this model, the immune response in a local microenvironment directed against allogeneic cells is assessed. Allogeneic (C3H mice) spleen cells were injected into the footpad of BALB/c mice and the draining popliteal lymph nodes were removed from the sacrificed mice four days later. By allogeneic stimulation, a specific immune response developed in the popliteal lymph node (Kroczek et al. *J. Immunol.* 139, 3597–3603 (1987), which was assessed by the increased lymph node mass, lymphocyte number, and in vitro lymphoproliferative response. Systemic administration of cyclosporin A has a marked inhibitory effect on the allogeneic immune response (Morris et al. *Transplant Proc.* 22, 1638–1641 (1990). When dialkyl $G_{M3}$ (10 nmol or 11 μg/mouse) was administered together with the allogeneic cells, a marked suppression of the immune response was observed (Table 2). This was evident as assessed by three parameters. First, there is a striking inhibition in the increase of lymph node mass. The net increase of lymph node mass in the mice of the control group stimulated with the allogeneic cells is 1.6 mg, the increase is only 0.45 mg when dialkyl $G_{M3}$ was coinjected with the allogeneic cells, which is very close to that for the systemically administered cyclosporin A (0.3 mg).

These results were confirmed by enumerating the total mononuclear cells recovered from the draining stimulated popliteal lymph nodes. The lymphocyte (Mononuclear-leukocyte) number is 0.8×10$^7$ for the dialkyl $G_{M3}$ treated group (five nodes from five mice), and 0.3×10$^7$ for the cyclosporin A treated group. These numbers are ≦⅓ of that of the control group (2.3×10$^7$ cells). Furthermore, the in vitro spontaneous proliferative assay by these recovered lymphocytes shows that dialkyl $G_{M3}$, like cyclosporin A, markedly suppresses the proliferation as measured by [$^3$H]thymidine incorporation under the conditions of three different cell densities (Table 2). For example, under the condition of 2×10$^5$ cells, the [$^3$H]thymidine uptake for the group of dialkyl $G_{M3}$ treatment is only 20% that of control group. Together, these results demonstrate substantial in vivo immunosuppressive activity of dialkyl $G_{M3}$.

TABLE 2

| PARAMETER | CONTROL | CYCLOSPORIN A | DIALKYL $G_{M3}$ |
|---|---|---|---|
| lymph node mass, mg[4] | | | |
| unstimulated | 1.17 ± 0.17 | 0.99 ± 0.34 | 1.41 ± 0.17 |
| stimulated | 2.77 ± 0.53 | 1.26 ± 0.22 | 1.86 ± 0.25 |
| net increase | 1.60 | 0.27 | 0.45 |
| lymphocytes ×10$^7$ [5] | 2.26 | 0.30 | 0.83 |
| [$^3$H]thymidine uptake, cpm[6] | | | |
| 2 × 10$^5$ cells | 1108 ± 18 | 201 ± 18 | 317 ± 45 |
| 1 × 10$^5$ cells | 372 ± 63 | 101 ± 4 | 152 ± 15 |
| 0.5 × 10$^5$ cells | 245 ± 53 | 63 ± 9 | 107 ± 29 |

[4]Allogeneic splenocytes (BALB/C, 2.5 × 106) were injected into the left hind footpad of C3H mice. In the group of dialkyl $G_{M3}$ treatment, 11 μg of dialkyl $G_{M3}$ was coinjected together with the allogeneic cells, which was compared with the systemic administration of CSA (24 mg/kg/day i.p. × 4 days). On day 4, the popliteal lymph nodes draining the left (stimulated) and the right footpad (unstimulated) were removed, and the lymph node mass measured. The data represent the mean ± SD of five mice in each group in this representative experiments. The difference between control and dialkyl $G_{M3}$ (or cyclosporin A) - treated groups is considered statistically significant, the P value is <0.01.
[5]The total mononuclear leukocytes recovered from five stimulated popliteallymph nodes of five mice in each group.
[6]The spontaneous lymphoproliferation was measured by [$^3$H]thymidine incorporation at three different cell density. The data represent the mean ± SEM of three cultures.

A SIMPLIFIED CARBOHYDRATE MOIETY-GANGLIOSIDE IS AN IMMUNOSUPPRESSANT

In this example a simplified carbohydrate moiety-ganglioside having the structure

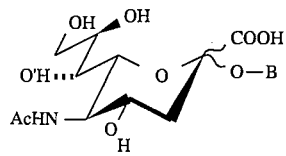

wherein B is

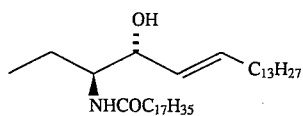

and wherein the stereochemistry indicated by wavy lines is either α or β was tested for its immunosuppressive properties. This simplified carbohydrate moiety-ganglioside is also referred to as $G_{M5}$ ($\alpha G_{M5}$ or $\beta G_{M5}$).

Materials and methods

Synthesis: The general synthesis strategy for synthesizing $G_{M5}$ is shown below:

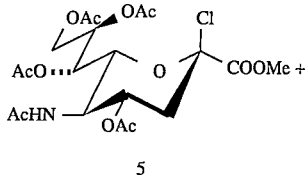

5

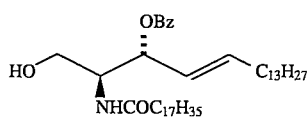

6

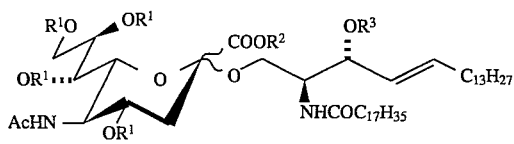

7 $R^1$ = Ac, $R^2$ = Me, $R^3$ = Bz (Bz = benzoyl)
8 $R^1$ = $R^2$ = $R^3$ = H

The bond indicated by a wavy line, indicates that the stereochemistry at that position may be either α or β. The synthesis of each is described below.

A. Synthesis of (2S,3R,4E)-3-O-Benzoyl-1-O-(methyl 5-acetamido-4,7,8,9-tetra-O-acetyl-3,5-dideoxy-D-glycero-a-and β-D-galacto-2-nonulopyranosylonate)-2-octadecanamido-4-octadecene-1,3-diol (7α and 7β).

Condensation of 6 (300 mg, 0.45 mmol) and 5 (460 mg, 0.9 mmol) in dichloromethane (5 mL) in the presence of Molecular sieves 4A (200 mg), 2,4,6-trimethylpyridine (0.16 mL) and silver triflate (385 mg), overnight at room temperature in the dark, gave 7α (133 mg, 26%) and 7β (159 mg, 31%), respectively, after column chromatography (silica gel, 30:1 CH2C12-MeOH).

B. Synthesis of (2S,3R,4E)-1-O-(5-acetamido-3,5-dideoxy-D-glycero-α- and β-D-galacto-f2-nonulopyranosylonicacid)-2-octadecanamido-4-octadecene-1,3-diol (8a and 8β). O-Deacylations of 7α(300 mg) and 7β(300 mg) were performed with a catalytic amount of sodium methoxide in methanol solution. Saponification of the methyl ester group was performed with 0.1M potassium hydroxide (0.43 mL) in methanol solution (3 mL) for 3 h at room temperature, to give 8α ($\alpha G_{M5}$) and 8β ($\beta G_{M5}$) in quantitative yields, respectively.

RESULTS

Immunosuppressive Activity of α and $\beta G_{M5}$ In Vitro: The immunosuppressive activity of α and $\beta G_{M5}$ were determined by the human lymphocyte proliferation assay as described above. Table 3 demonstrates that both α and $\beta G_{M5}$ are potent immunosuppressive agents. $\alpha G_{M5}$ exhibits 99% inhibition of human lymphoproliferation at both 2.5 and 5.0 nM. $\beta G_{M5}$ exhibits slightly less inhibition: 86% at 2.50 μM and 97% at 5.0 μM.

TABLE 3

|  | [$^3$H] Thymidine Uptake CPM × 10$^{-3}$ | | Inhibition (%) | |
|---|---|---|---|---|
|  | 2.5 μM | 5.0 μM | 2.5 μM | 5.0 μM |
| control | 9.8 | 9.8 |  |  |
| $G_{M3}$ |  |  |  |  |
| d18:1-C14:0 $G_{M5}$ (d18:1-C18:0) | 4.6 | 0.8 | 53 | 92 |
| αsialosyl ceramide | 0.1 | 0.1 | 99 | 99 |
| βsialosyl ceramide | 1.4 | 0.3 | 86 | 97 |
| dialkyl $G_{M3}$ | 0.7 | 0.3 | 93 | 97 |

In addition the ID90 of $\alpha G_{M5}$ was determined to be ≈2.5 μM (FIG. 8).

Immunosuppressive Activity of $\alpha G_{M5}$ In Vivo: The ability of $\alpha G_{M5}$ to inhibit the alloimmune response in draining popliteal lymph nodes in vivo (as described above) was determined (Table 4). $\alpha G_{M5}$ was formed to be highly immunosuppressive in vivo as compared to systemically administered cyclosporin A (CSA). $\alpha G_{M5}$ caused a ⅔ reduction in cellular immune response (the increase in lymph mass caused by in vivo allostimulation).

TABLE 4

|  | lymph node mass, mg$^7$ | | |
|---|---|---|---|
|  | Unstimulated | stimulated | net increase |
| Control | 1.30 ± 0.28 | 2.93 ± 0.81 | 1.63 |
| CSA | 0.67 ± 0.06 | 0.85 ± 0.21 | 0.18 |
| $G_{M5}$ α Sialosyl ceramide | 0.82 ± 0.26 | 1.40 ± 0.22 | 0.58 |

[7]Allogeneic splenocytes (BALB/C, 2.5 × 106) were injected into the left hind footpad of C3H mice. In ganglioside-treated group, 10 nmol of each ganglipsides were coinjected together with the allogeneic cells, which was compared with the systemic administration of CSA (24 mg/kg/dose i/i.p. × 4 doses). On day 4, the popliteal lymph nodes draining the left (stimulated) and the right footpad (unstimulated) were removed, and the lymph node mass measured. The data represent the mean ± SD of five mice in each group in this representative experiment. The difference between control and ganglioside (or cyclosporinA)-treated groups is statistically significant, the P value is <0.01.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated wherein, but is only limited by the following claims.

What is claimed is:

1. A compound having the formula

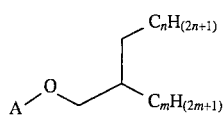

wherein A is a carbohydrate moiety which corresponds to the carbohydrate moiety of a naturally occurring ganglioside, n is 5 to 20 and m is 5 to 20.

2. A compound according to claim 1 wherein n is 13 and m is 14.

3. A compound according to claim 1 wherein A is

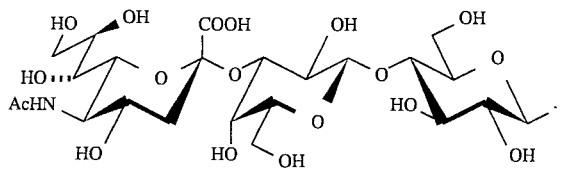

4. A compound according to claim 3 wherein n is 13 and m is 14.

5. A composition of matter comprising a compound having the formula

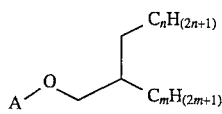

wherein A is a carbohydrate moiety which corresponds to the carbohydrate moiety of a naturally occurring ganglioside, n is 5 to 20 and m is 5 to 20 and a pharmaceutically acceptable carrier for said compound.

6. A composition of matter according to claim 5 wherein n is 13 and m is 14.

7. A composition of matter according to claim 5 wherein A is

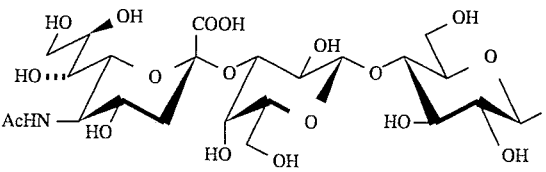

8. A composition of matter according to claim 7 wherein n is 13 and m is 14.

9. A method of suppressing an immune response in an animal comprising the step of administering an immune response suppressing effective amount of a compound having the structure:

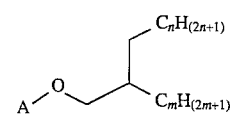

wherein A is a carbohydrate moiety, which corresponds to the carbohydrate moiety of a naturally occurring ganglioside, n is 5 to 20 and m is 5 to 20.

10. A method of suppressing an immune response in an animal according to claim 9 wherein n is 13 and m is 14.

11. A method of suppressing an immune response in an animal according to claim 9 wherein A is

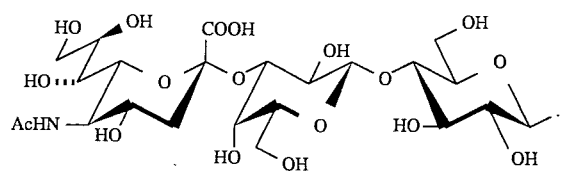

12. A method of suppressing an immune response in an animal according to claim 11 wherein n is 13 and m is 14.

* * * * *

UNITED STATES PATENT AND TRADEMARK OFFICE
CERTIFICATE OF CORRECTION

PATENT NO. : 5,567,684
DATED : October 22, 1996
INVENTOR(S) : Ladisch et al.

It is certified that error appears in the above-indentified patent and that said Letters Patent is hereby corrected as shown below:

In Column 1, before "BACKGROUND OF THE INVENTION" the following Government acknowledgment should be inserted: -- This invention was made with Government support under Grant No. CA 42361, awarded by the National Institutes of Health. The Government has certain rights in this invention. --

Signed and Sealed this

First Day of June, 1999

Attest:

Attesting Officer

Q. TODD DICKINSON

Acting Commissioner of Patents and Trademarks